United States Patent [19]

Mahurkar

[11] Patent Number: 4,895,561
[45] Date of Patent: Jan. 23, 1990

[54] DUAL-LUMEN CATHETER-CONNECTING SYSTEM

[76] Inventor: Sakharam D. Mahurkar, 6171 N. Sheridan Rd., Suite 1112, Chicago, Ill. 60660

[21] Appl. No.: 194,143

[22] Filed: May 16, 1988

[51] Int. Cl.$^4$ .......................................... A61M 25/00
[52] U.S. Cl. ...................................... 604/43; 604/53; 604/283; 604/174
[58] Field of Search .................... 604/280, 283, 43-45, 604/284, 281, 250, 174, 179

[56] References Cited

U.S. PATENT DOCUMENTS

| | | | |
|---|---|---|---|
| 3,256,885 | 6/1966 | Higgins et al. | 604/281 |
| 3,812,851 | 5/1974 | Rodriguez | 604/179 |
| 4,557,261 | 12/1985 | Rugheimer | 604/283 |
| 4,626,240 | 12/1986 | Edelman et al. | 604/43 |
| 4,643,711 | 2/1987 | Bates | 604/43 |
| 4,682,978 | 7/1987 | Martin | 604/283 |

*Primary Examiner*—Stephen C. Pellegrino
*Attorney, Agent, or Firm*—Stephen G. Rudisill

[57] ABSTRACT

A dual-lumen catheter assembly comprising a dual-lumen catheter, a Y connector having one end fastened to the proximal end of the catheter, and a pair of extension tubes each having one end fastened to the opposite end of the connector from the catheter, each of the extension tubes being bent back toward the distal end of the catheter, extending along opposite sides of the connector.

53 Claims, 5 Drawing Sheets

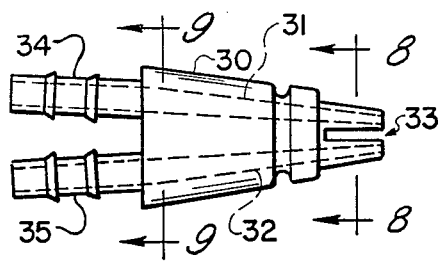
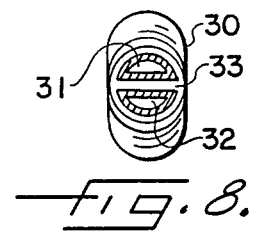
Fig. 8.
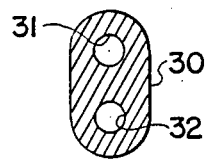
Fig. 9.
Fig. 7.
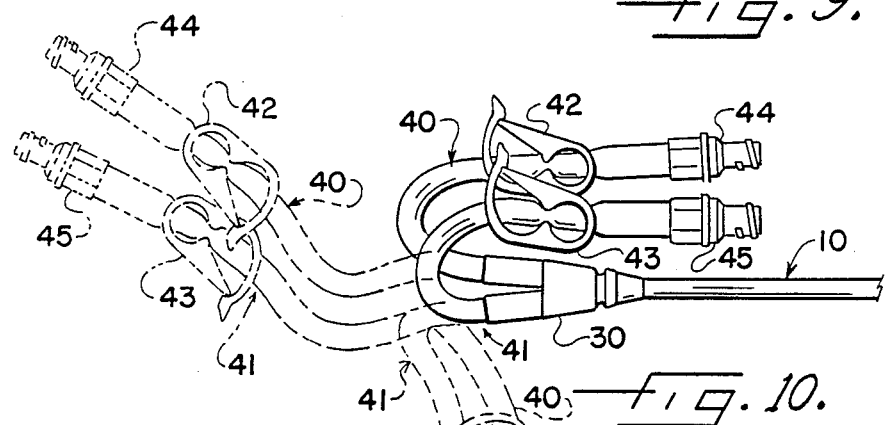
Fig. 10.
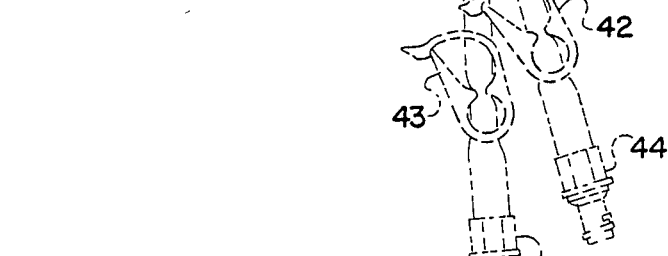
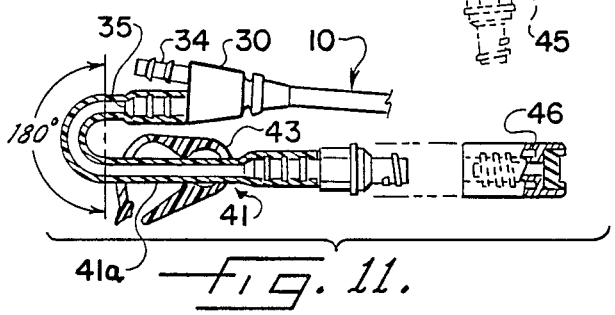
Fig. 11.

DUAL-LUMEN CATHETER-CONNECTING SYSTEM

FIELD OF THE INVENTION

The present invention relates generally to extracorporeal blood treatment systems and, more particularly, to an improved method and apparatus for connecting a dual-lumen catheter to the long flexible tubes whic carry blood in both directions between the catheter and an extracorporeal blood treatment unit. This invention is particularly concerned with such a method and apparatus which permits the catheter to be positioned in convenient anatomical sites during the periods between successive treatments to avoid patient discomfort and accidental displacement of the catheter, and to facilitate sterile attachment of the catheter to the patient during such periods.

BACKGROUND OF THE INVENTION

Dual-lumen catheters have come into widespread use for extracorporeal blood purification procedures such as hemodialysis. Blood is withdrawn from the patient through one of the lumens of the catheter and supplied to a hemodialysis unit where the blood is purified, and the resulting purified blood is then returned to the patient through the other lumen of the catheter. Examples of such catheters are shown in U.S. Pat. Nos. 4,134,402; 4,583,968; and 4,682,978.

Although these catheters were originally intended for acute hemodialysis treatments, the catheters have proven to be so satisfactory that they are typically allowed to remain in patients for several weeks, and sometimes for several months. The catheters are used for the hemodialysis treatments that such patients receive approximately every three days, and during the interdialytic periods the catheter remains inserted in and attached to the patient.

Dual-lumen hemodialysis catheters are normally supplied with certain auxiliary components permanently pre-attached to the catheter. These auxiliary components facilitate the connection of the two lumens of the catheter (which are extremely small within the catheter) to a pair of long flexible tubes which carry blood to and from the hemodialysis unit. The auxiliary components include a Y-shaped hub which receives the proximal end of the catheter at one end of the hub, and a pair of extension tubes which are fastened to the opposite end of the hub and carry a pair of clamps, female luer fittings for connection to male luer fittings on the long tubes leading to the hemodialysis unit, and a pair of caps (usually with injectable elastomeric ports) closing the openings of the luer fittings.

The hub and portions of the extension tubes affixed to the catheter are normally used to secure the catheter to the patient, by the use of sutures and by applying tape or an adhesive-coated bandage across the hub and/or the extension tubes and adhering the tape or bandage to the skin of the patient on opposite sides of the hub. Sometimes the hub forms either a suture groove or a suture web or "wing" to facilitate attachment to the patient by suturing. Because of the length of the extension tubes and the other auxiliary components, the extracorporeal part of the catheter assembly usually extends beyond the patient's body. As a result, the catheter is continually disturbed by movements of the patient and/or people and equipment around the patient, or by clothing which is periodically donned or removed by the patient. It is not unusual for such movements to cause the catheter to become dislodged entirely from the patient. Even when the catheter is not dislodged, continual movement of the catheter within the vein causes discomfort and pain to the patient, and can lead to damage to the vein in which the catheter is inserted.

For example, when the catheter is inserted in a jugular vein, the extension tubes normally extend upwardly along the neck and ear of the patient. This not only makes it difficult to attach the catheter to the patient (sometimes the hub or extension tubes are taped to the ear or even around the entire neck or head of the patient), but also places both the hub and the extension tubes in the direct path of movement of the patient's head. When the catheter is inserted into a subclavian vein, which is located under the clavicle, the extension tubes typically project upwardly or outwardly beyond the shoulder of the patient.

Regardless of where the catheter is located on the patient's body, the weight of the long tubes leading to the dialysis unit, which typically have a larger cross section than the extension tubes, often exerts pulling forces on the extension tubes and the catheter, which of course tends to withdraw the catheter from the patient's body. These forces are also applied to the sutures, causing discomfort and pain to the patient, and can cause the catheter to pivot back and forth within the vein, thereby irritating the walls of the vein. Such catheter movements can also cause suction forces to be exerted on the vein walls.

SUMMARY OF THE INVENTION

It is a primary object of the present invention to provide an improved dual-lumen catheter-connecting system which permits the catheter to remain relatively stable during the entire time the catheter remains inserted in the patient, even during long-term use of the catheter extending over numerous extracorporeal blood treatments. In this connection, related objects of the invention are to provide such a catheter-connecting system which significantly improves the comfort level of the patient in whom the catheter is inserted, and which greatly reduces the risk of venous damage.

A more specific object of the invention is to provide an improved dual lumen catheter system which enables the catheter to be secured to the body of the patient in natural anatomical depressions, or fossa, where the extracorporeal portions of the catheter assembly are shielded by the patient's body. In these regions the catheter is not easily disturbed by movements of the patient or by movement of people and articles around the patient, regardless of the particular vein into which the catheter is inserted. In this connection, a related object is to provide such a system which facilitates the donning and removal of clothing by the patient, and which enables ambulatory patients to wear normal clothing, without any unsightly or embarrasing projections, between successive extracorporeal blood treatments.

Another important object of this invention is to provide an improved hemodialysis catheter-connecting system which facilitates connection of the catheter and its attached auxiliary components to the long flexible tubes which lead to the dialysis unit, regardless of where the dialysis unit is positioned relative to the patient.

One specific object of the invention is to eliminate the need to attach the auxiliary components of a dual-lumen catheter, to the neck, ears or head of the patient when the catheter is inserted in a jugular vein, and which discourages the use of bandages or tape encircling the neck of the patient.

A further object of the invention is to reduce the area that must be covered with a bandage around the proximal end of the catheter in order to maintain sterile conditions around the access site.

Yet another object of the invention is to facilitate connection of a dual-lumen hemodialysis catheter to a hemodialysis unit located anywhere around the patient.

A still further object of the invention is to provide an improved catheter-connecting system which to a large extent isolates the catheter from retracting forces and bending moments applied to the extension tubes, thereby reducing movement of the catheter tip within the vein and consequently reducing initiation and suction forces on the vein walls. A related specific object is to eliminate any projection of the auxiliary components of the catheter beyond the extremity of the shoulder of the patient when the catheter is inserted into the subclavian vein of the patient.

It is another object of the invention to provide such a system which avoids kinking of the extension tubes and helps prevent collapse and maintain patency of the extension tubes A further object is to avoid the exertion of pulling forces, due to the weight of the dialysis tubes, on the catheter, and to reduce such forces on the sutures attaching the catheter assembly to the patient.

BRIEF DESCRIPTION OF THE DRAWINGS

Other objects and advantages of the invention will become apparent upon reading the following detailed description and upon reference to the drawings in which:

FIG. 7 is a plan view of the Y-shaped hub of the catheter assembly of FIG. 1;

FIG. 8 is a section taken generally along line 8—8 in FIG. 7;

FIG. 9 is a section taken generally along line 9—9 in FIG. 7;

FIG. 10 is a fragmentary side elevation of the catheter assembly of FIG. 1, illustrating the extension tubes in three different positions;

FIG. 11 is a partial side elevation and partial sectional view of one of the extension tubes and the auxiliary components associated therewith in the catheter assembly of FIG. 1;

Figure 1:
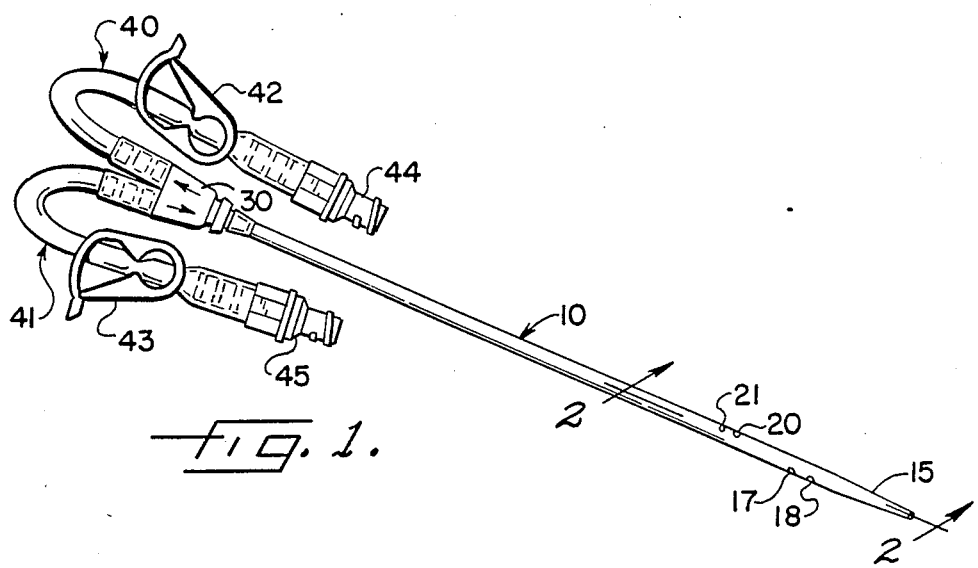
FIG. 1 is a perspective view of a dual-lumen hemodialysis catheter assembly embodying the present invention.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF PREFERRED EMBODIMENTS

Figure 2:
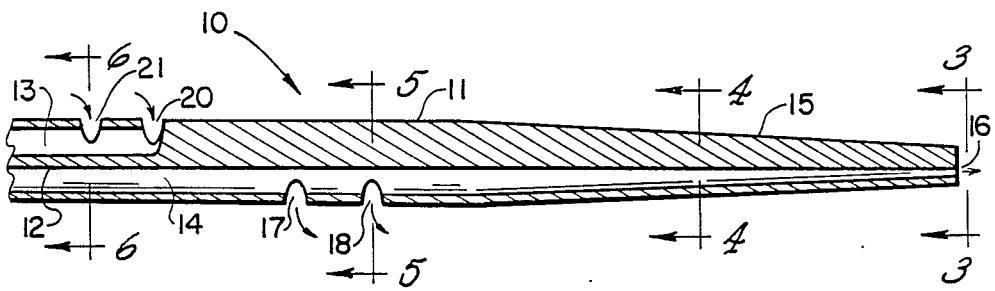
FIG. 2 is an enlarged longitudinal section taken along a diameter of the distal portion of the catheter of FIG. 1, perpendicular to the septum inside the catheter, as generally illustrated by line 2—2 in FIG. 1.
Figures 3, 4, 5, 6:
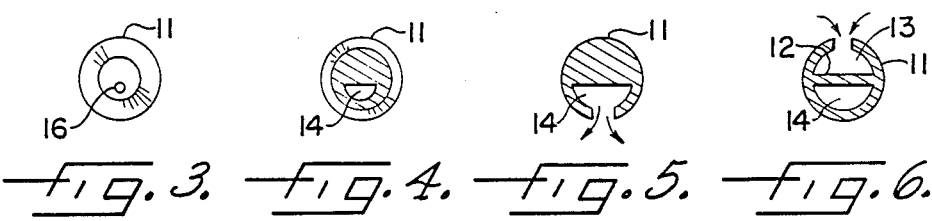
FIG. 3 is an end elevation taken at the distal end of the catheter portion shown in FIG. 2 as illustrated by line 3—3 in FIG. 2.
FIG. 4 is a section taken generally along line 4—4 in FIG. 2.
FIG. 5 is a section taken generally along line 5—5 in FIG. 2.
FIG. 6 is a section taken generally along line 6—6 in FIG. 2.

Turning no to the drawings and referring first to FIG. 1, there is shown a dual-lumen hemodialysis catheter 10 of the type described in Mahurkar U.S. Pat. No. 4,583,968, issued Apr. 22, 1986 for "Smooth Bore Double Lumen Catheter". This catheter 10 has a cylindrical body portion 11 which is hollow except for a flat, longitudinal, diametral septum 12 which divides the interior of the hollow cylinder into two parallel lumens 13 and 14, each having a D-shaped cross section (FIGS. 2 and 3). As illustrated by the arrows in FIG. 2, the lumen 13 is the blood-intake lumen, and the lumen 14 is the blood-return lumen.

At the distal end of the catheter, the exterior surface of the cylinder 11 merges into a smoothly tapered conical tip 15. On the inside, the blood return lumen 14 extends longitudinally all the way through the tip 15, bending slightly as its passes through the tip so that it opens at 16 near the center of the distal end of the conical tip, as can be seen in FIGS. 2 and 3. Within the tip 15, the cross-sectional shape of the lumen 14 gradually changes from D-shaped at the proximal end of the tip 15 (see FIG. 5) to circular at the distal end of the tip (see FIG. 3). An intermediate configuration of the transition from D to circular is shown in the sectional view in FIG. 4.

In addition to the opening 16 at the distal end of the blood-return lumen 14, a pair of additional apertures 17 and 18 are formed in the side wall of the return lumen. These two apertures 17 and 18 are spaced longitudinally away from the distal opening 16 toward the proximal end of the catheter. These apertures ensure the flow of blood through the return lumen 14 even in situations where the distal opening 16 might become wholly or partially blocked.

In order to provide a longitudinal spacing between the distal openings of the two lumens 13 and 14, the blood intake lumen is terminated at an opening 20 in the side wall of the catheter. A second opening 21 spaced longitudinally from the opening 20 permits blood to enter the lumen 13 in the event of a blockage of the opening 20 against the wall of the vein into which the catheter 10 is inserted.

At the proximal end of the catheter 10, the two D-shaped lumens 13 and 14 open into a Y-shaped connector or hub 30 which forms two internal passageways 31 and 32 (see FIGS. 7–9) communicating with the proximal ends of the catheter lumens. As can be seen in FIGS. 7 and 8, the distal ends of the hub passageways 31 and 32 are D-shaped and are separated by a thin gap 33 for receiving the septum 12 of the catheter. The walls of the catheter lumens are expanded at the proximal end of the catheter to fit over the corresponding portions of the hub 30, as shown in FIG. 1, and the inside walls of the catheter lumens are preferably bonded to the mating walls of the hub 30. The passageways 31 and 32 then diverge from each other and assume a circular cross section (see FIG. 9) as they extend toward the proximal end of the hub, and they also increase in cross-sectional area, as can be seen in FIG. 7. At the proximal end of the hub 30, the hub passageways 31 and 32 open into a pair of ferrules 34 and 35 formed as integral parts of the hub.

To facilitate connection of the catheter hub 30 to the conventional tubes leading to a dialysis unit, and also to accommodate a pair of clamps for opening and closing the blood intake and return passageways, a pair of extension tubes 40 and 41 are attached to the ferrules 34 and 35 on the proximal end of the hub 30. These extension tubes 40 and 41 are typically formed of a polymeric material such as silicone, and are long enough to receive a pair of conventional clamps 42 and 43 for opening and closing the respective tubes. The clamps 42 and 43 serve as on-off valves or flow control devices for controlling the flow of blood between the catheter and the dialysis unit.

The distal ends of the extension tubes 40 and 41 are permanently attached to the Y connector, and the proximal ends of the tubes are permanently bonded to a pair of female luer fittings 44 and 45 which match the male luer fittings conventionally provided on the ends of the tubes leading to the dialysis unit. The mating luer fittings serve as coupling means for coupling the proximal ends of the extension tubes to the flexible tubes leading to the extracorporeal blood treatment unit. The extension tubes 40 and 41 are relatively soft and flexible, so that they can be easily manipulated and also easily closed by the pressure of the clamps 42 and 43.

In accordance with one important aspect of the present invention, the extension tubes are bent back toward the distal end of the catheter, preferably extending along the sides of the catheter and the Y-shaped hub. By providing these U-bends in the extension tubes, the auxiliary connecting elements attached to the proximal end of the catheter can be accommodated in a small area around the access site on the patient's body. Consequently, the entire connecting assembly for the catheter, including the luer fittings on the proximal ends of the extension tubes, can be located on a protected portion of the patient's body. There are no projections to interfere with movements of the patient, or with the movement of people and articles around the patient. It is also easy for the patient to don and remove clothing, and normal clothing can be worn by the patient during interdialytic periods without any unsightly or embarrassing projecting portions of the catheter assembly.

Perhaps even more importantly, any forces exerted on the proximal ends of the extension tubes tend to move the catheter in a direction opposite that of the applied force. Thus, when pulling forces are exerted on the extension tubes by the long and relatively heavy tubes leading to the dialysis unit, for example, those forces tend to push the catheter into the patient to hold it in place, rather than withdrawing the catheter. Consequently, the risk of accidental dislodgement of the catheter is greatly reduced, as is the risk of vein irritation and damage.

In the particular embodiment illustrated in the drawings, the U-bend in each extension tube 40 and 41 begins at a point just slightly beyond the proximal end of the hub ferrule 34 or 35 (see FIG. 11). The bend is exactly 180°, and terminates in a straight length of tubing 40a or 41a which is long enough to receive one of the clamps 42 and 43 and the stem of the luer fitting 44 or 45 and its cap 46 (see FIG. 11).

In accordance with one particular aspect of the invention, the U-bends are permanently formed in the extension tubes 40 and 41. That is, both the overall shape of the bend and the size of the interior passageway of the bend are set or "memorized" in the extension tube so that the tube always returns to that configuration. The U-bends are still flexible but are substantially stiffer than the straight end portions of the tubes, as a result of which any forces applied to the more flexible end portions of the tubes tend to simply pivot those flexible end portions about the relatively stiff bent portions. Consequently, the catheter is to a large extent isolated from bending moments applied to the end portions of the extension tubes. This greatly reduces pivoting and tilting movement of the catheter within the vein, thereby further reducing irritation of the vein walls and the attendant risk of venous damage.

The relatively stiff U-bends also form a fulcrum about which the proximal portions of extension tubes can be turned to facilitate connection to a dialysis unit located anywhere within a 360° circle around the patient. This flexibility of the catheter assembly is illustrated in FIG. 10, which shows the extension tubes bent laterally to one side of the catheter in solid lines, to the other side in dashed lines, and in a direction away from the catheter in phantom lines.

With certain silicones and other polymeric materials, the extension tubes 40 and 41 may be set in the desired size and shape by simply heating each tube while holding it in the desired size and shape. One simple and effective way to accomplish this is to slide the extension tube over a U-shaped wire or rod which defines the radius of the desired bend and also the size of the interior passageway to be maintained within the bend. The curved portion of the tube, with the wire still in place, is then dipped in a liquid heated to a temperature sufficient to set, i.e., effect cross linking of, the polymer. Alternatively, the bent portions of the extension tubes can be molded or otherwise formed from a polymer that has a greater durometer than the straight sections of the tubes.

Figure 12:
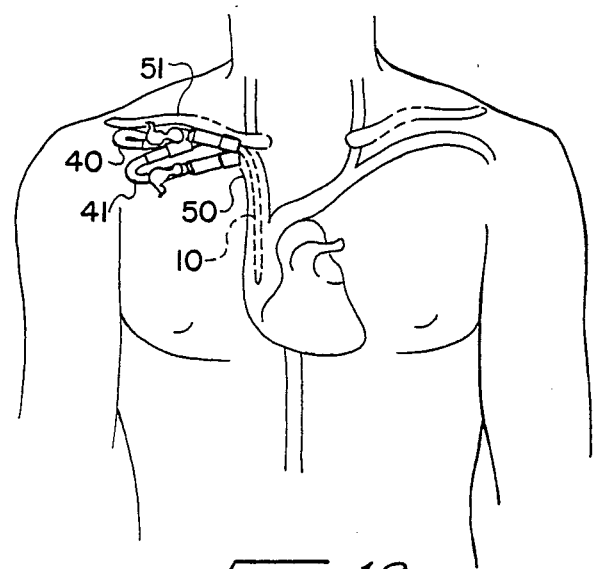
FIG. 12 is a diagrammatic view of a portion of a human body with the catheter of FIG. 1 inserted in a subclavian vein.

FIG. 12 illustrates the catheter of FIG. 1 inserted in a subclavian vein 50 of a patient. It can be seen that the access site for the catheter 10 is located adjacent the clavicle 51 of the patient, and the catheter is inserted in a direction generally parallel to the clavicle 51. Thus, the distal portions of the extension tubes 40 and 41 connected to the Y-shaped hub 30 extend outwardly from the hub 30 toward the outer extremity of the shoulder of the patient. Because of the U-bends in the extension tubes, however, the extension tubes 40 and 41 curve back toward the center of the patient's body before they reach the outer extremity of the shoulder. The luer connections to the long tubes leading to the dialysis unit are consequently located close to the access site. As a result, the entire catheter assembly is nestled in a relatively small region around the access site, in the infraclavicular fossa, where the catheter and its auxiliary components ar sheltered by the body of the patient from people and articles moving around the patient. No portion of the catheter assembly projects beyond the body of the patient, nor interferes with movements of the patient. When the tubes leading to the dialysis unit are disconnected from the luer fittings on the catheter assembly, an ambulatory patient can move freely about with little concern about snagging the catheter assembly on clothing or other articles.

Figure 13:
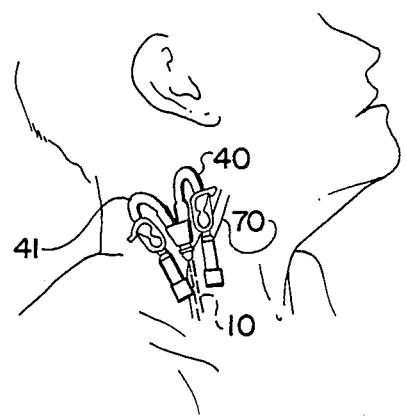
FIG. 13 is a diagrammatic view of a portion of a human body having the catheter of FIG. 1 inserted in a jugular vein.

FIG. 13 illustrates a patient having the catheter assembly of FIG. 1 inserted in a jugular vein 70. It can be seen that the access site to the jugular vein 70 is located at the base of the neck of the patient, and the catheter 10 is inserted downwardly into the jugular vein. Consequently, the straight distal portions of the extension tubes 40 and 41 extend upwardly along the lower portion of the patient's neck. Because of the presence of the U-bends in the extension tubes, the straight proximal portions of the extension tubes 40 and 41 bend back down along the lower portion of the patient's neck so that the luer fittings are located near the access site. Here again, the entire catheter assembly ends up being located in a compact area where it is well protected in the cervical triangle of the patient's body.

Figure 14:
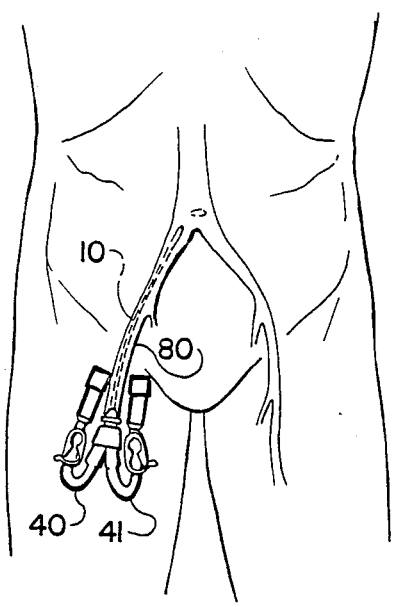
FIG. 14 is a diagrammatic view of a portion of a human body having the catheter of FIG. 1 inserted in a femoral vein.

FIG. 14 illustrates a patient having the catheter assembly of FIG. 1 inserted in a femoral vein 80. The catheter is inserted upwardly into the femoral vein 80 along the patient's thigh. The distal ends of the extension tubes 40 and 41 then extend downwardly along the thigh but, because of the presence of the U-bends in the extension tubes, the proximal ends of the tubes curve upwardly along the thigh. Consequently, the catheter assembly does not interfere with surrounding organs and leg movements of the patient. Moreover, the catheter assembly remains snugly attached to the patient in the well protected femoral triangle region of the body.

Figure 15:
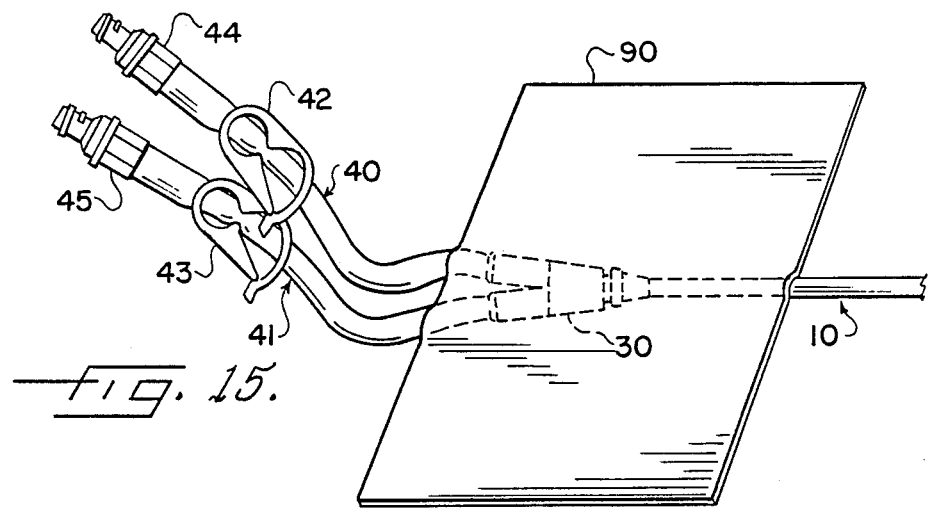
FIG. 15 is a perspective view of the first tier of a two-tier attachment system for the catheter assembly of FIG. 1.
Figure 16:
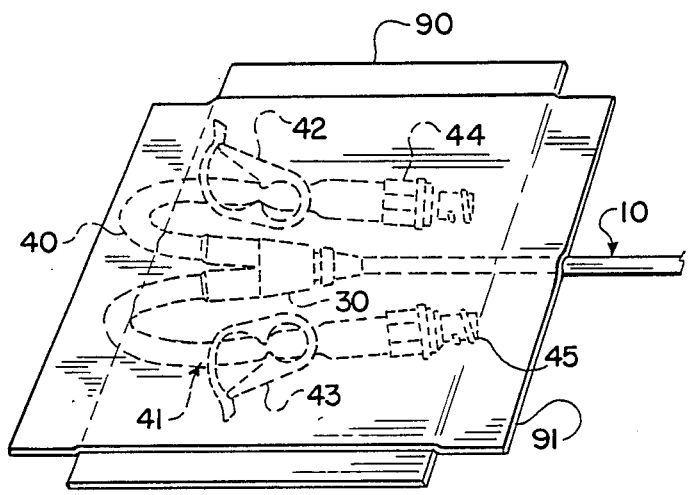
FIG. 16 is a perspective view of a two-tier attachment system for the catheter of FIG. 1, including the first tier shown in FIG. 15.

FIGS. 15 and 16 illustrate a preferred two-tier arrangement for attaching the catheter assembly to the patient. In this arrangement, the access site, the hub 30, and the straight distal portions of the extension tubes 40 and 41 are attached to the patient by an adhesive bandage 90 as illustrated in FIG. 15. The straight proximal portions of the extension tubes, including the clamps and luer fittings carried thereby, are then placed on top of the bandage 90 and fastened by a second bandage 91 so that they are held securely in place on the top surface of the bandage 90. The bandage 90 is thus used to protect the patient from abrasion due to rubbing of the clamps and/or the luer fittings on the skin of the patient, and also isolates the Y connector from the movements of the extension tubes during dialysis.

Figure 17:
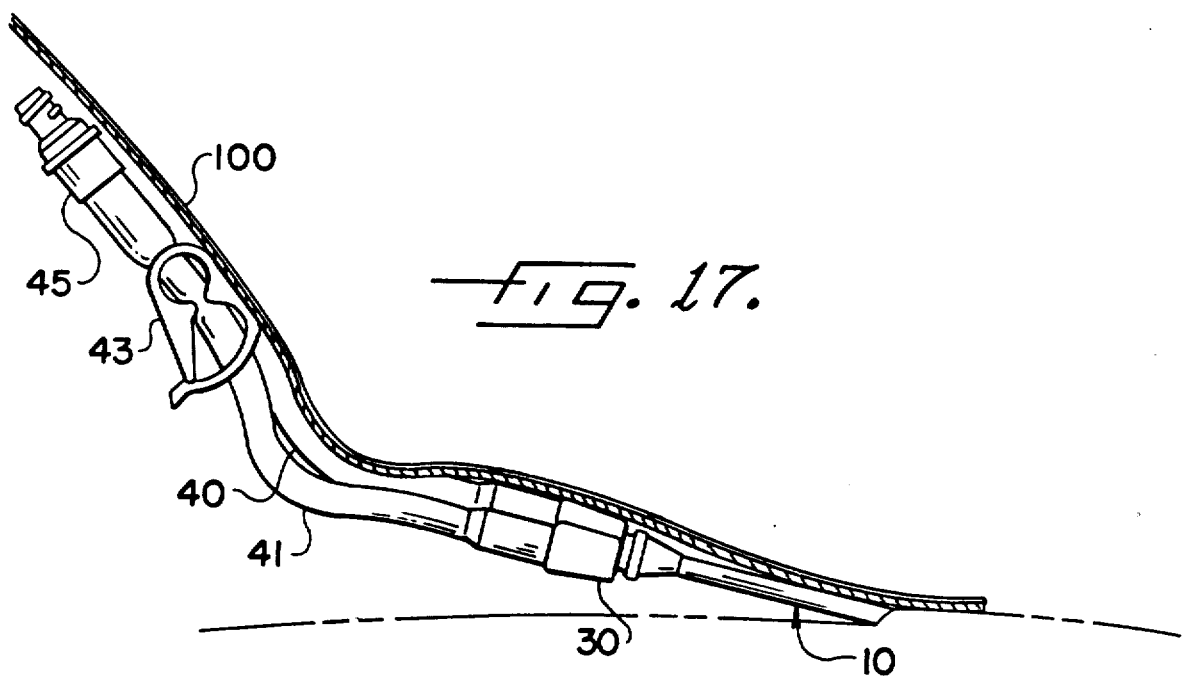
FIG. 17 is a partial side elevation and partial sectional view of an alternative attachment system for the catheter of FIG. 1.
Figure 18:
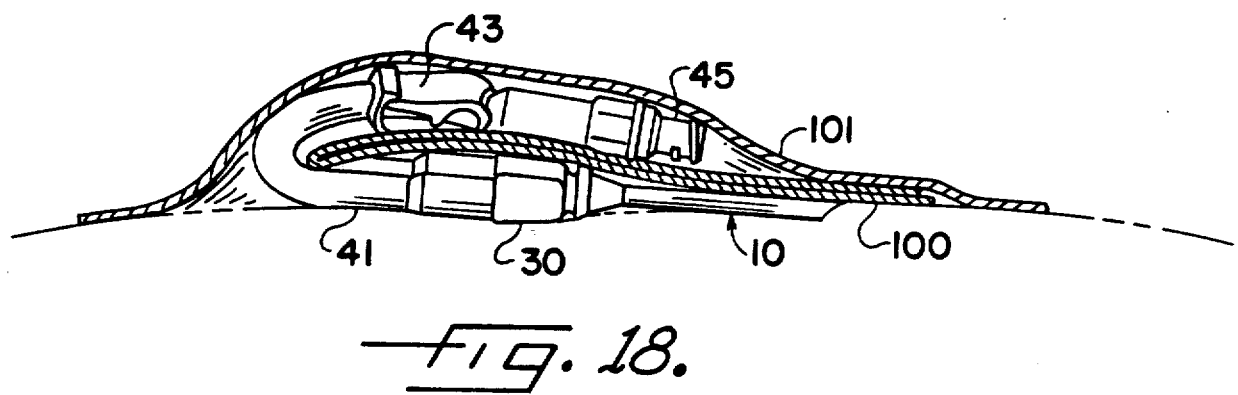
FIG. 18 is a partial side elevation and partial sectional view of the attachment system shown in FIG. 17 with the catheter assembly in a closed condition.

FIGS. 17 and 18 illustrate an alternative attachment technique which also seals the open ends of the luer fittings on the catheter assembly. As illustrated in FIG. 17, a first length of tape 100 is applied along one side of the catheter assembly, with the U-bends in the extension tubes straightened out. Then when the extension tubes are allowed to relax, returning the extension tubes to their normal U-shaped configuration, the tape 100 bends on itself to hold the catheter assembly firmly in position in its relaxed condition. Next, a second length of tape 101 is applied over the catheter assembly, with the portion of the tape 101 that extends beyond the luer fittings adhering to the first tape 100. This forms a relatively tight seal around the open ends of the luer fittings, preventing the entry of bacteria into the catheter assembly. The second length of tape 101 is adhered to the body of the patient to hold the entire catheter assembly securely in place in the desired location on the patient's body.

While the invention has been described with specific reference to the use of permanently bent extension tubes, the curved passageways provided by those extension tubes may instead be formed by a unitary connecting member fastened to the proximal end of the dual-lumen catheter. More specifically, the unitary connecting member may form two internal U-shaped passageways, each of which is in communication with one of the lumens of the catheter. The other ends of the passageways may terminate in a pair of integral ferrules for direct connection to a pair of tubes leading to the dialysis unit, or the passageways may lead into a pair of straight extension tubes carrying the conventional clamps and luer fittings. Because the internal passageways are U-shaped, curving back toward the distal end of the catheter, any forces applied to the unitary connecting member by tubes leading to the dialysis unit will tend to move the catheter in a direction opposite that of the applied forces. Consequently, pulling forces exerted on the connecting member will tend to hold an inserted catheter in place rather than withdrawing it.

I claim:

1. A dual-lumen catheter assembly comprising:
   a dual-lumen catheter having a distal end and a proximal end,
   flow diversion means having one end fastened to the proximal end of said catheter, and
   a pair of flexible extension tubes each having one end fastened to the opposite end of said flow diversion means from said catheter, each of said extension tubes being bent back toward the distal end of said catheter to form a bend having a predetermined shape, each bend being adapted to flex and deform from said predetermined shape in response to an external force and being adapted to return to said predetermined shape in response to removal of said external force.

2. The catheter assembly of claim 1 wherein said extension tubes, including the bends therein, are flexible.

3. The catheter assembly of claim 1 wherein the bent extension tubes and the flow diversion means lie in substantially the same plane.

4. The catheter assembly of claim 1 which includes a pair of luer fittings fastened to the proximal ends of said extension tubes, and a closure cap on each of said luer fittings.

5. The catheter assembly of claim 1 wherein said connector includes a pair of ferrules on said opposite end thereof, and said extension tubes are fastened to said ferrules.

6. The catheter assembly of claim 1 which includes flow control means on each of said extension tubes, on the proximal sides of said bends in said tubes.

7. The catheter assembly of claim 1 wherein said flow diversion means includes a pair of internal passageways communicating with the dual lumens of said catheter at said one end of said flow diversion means and with said extension tubes at said opposite end of said flow diversion means.

8. The catheter assembly of claim 1 wherein the bends in said extension tubes are generally U-shaped.

9. The catheter assembly of claim 1 wherein said dual-lumen catheter comprises a cylindrical body portion having an internal longitudinal septum forming a pair of elongated lumens having D-shaped cross sections, the distal end of said body portion terminating in a smooth conical tapered tip, one of said lumens extending longitudinally through said tip, and the other lumen terminating at an opening formed in the side wall of said catheter proximally of the distal end of said tip.

10. A blood treatment system comprising
a dual-lumen catheter having a distal end and a proximal end,
flow diversion means having one end fastened to the proximal end of said catheter,
a pair of flexible extension tubes each having one end fastened to the opposite end of said flow diversion means from said catheter, each of said extension tubes being bent back toward the distal end of said catheter to form a bend having a predetermined shape, each bend being adapted to flex and deform from said predetermined shape in response to an external force and being adapted to return to said predetermined shape in response to removal of said external force,
a blood treatment unit for receiving blood withdrawn from a patient through one of the lumens of said catheter, purifying the withdrawn blood, and returning the purified blood to the patient through the other lumen of said catheter,
a pair of flexible tubes connecting said extension tubes to said blood treatment unit,
flow control means for controlling the flow of blood between said catheter and said blood treatment unit, and
coupling means for coupling the proximal ends of said extension tubes to said flexible tubes.

11. The system of claim 10 wherein said catheter is inserted into a patient and which includes a bandage fastening said flow diversion means to the skin of the patient, with the portions of said extension tubes on the proximal sides of said bends positioned on top of said bandage.

12. The system of claim 11 which includes means fastening to the top of said bandage the portions of said extension tubes on the proximal sides of said bends.

13. The system of claim 11 which includes flow control means and luer fittings installed, said extension tubes on the proximal sides of said bends.

14. The system of claim 10 wherein said extension tubes, including said bends, are flexible.

15. The system of claim 11 wherein the bent extension tubes and said flow diversion means lie in substantially the same plane.

16. The system of claim 10 which includes a pair of luer fittings fastened to the proximal ends of said extension tubes, and a closure cap on each of said luer fittings.

17. The system of claim 10 wherein said connector includes a pair of ferrules on said opposite end thereof, and said extension tubes are fastened to said ferrules.

18. The system of claim 10 which includes flow control means on each of said extension tubes, on the proximal sides of said bends in said tubes.

19. The system of claim 10 wherein said flow diversion means forms a pair of internal passageways coimmunicating with the dual lumens of said catheter at said one end of the connector and with said extension tubes at said opposite end of the connector.

20. The system of claim 10 wherein the bends in said extension tubes are generally U-shaped.

21. A method of preparing a patient for extracorporeal blood treatment comprising the steps of inserting into a vein selected from the group consisting of the jugular, subclavian and femoral veins of the patient, the distal end portion of a dual-lumen catheter assembly having
flow diversion means having one end fastened to the proximal end of said catheter,
a pair of flexible extension tubes each having one end fastened to the opposite end of said flow diversion means from said catheter, each of said extension tubes being bent back toward the distal end of said catheter and extending alongside said flow diversion means to form a bend having a predetermined shape, each bend being adapted to flex and deform from said predetermined shape in response to an external force and being adapted to return to said predetermined shape in response to removal of said external force,
flow control means for controlling the flow of blood between said dual-lumen catheter and an extracorporeal blood treatment unit, and
coupling means for coupling said extension tubes to said blood treatment unit, and
taping said flow diversion means and extension tubes to the skin of the patient.

22. The method of claim 21 wherein said flow diversion means and extension tubes are attached to the skin of the patient by a bandage, and the portions of said extension tubes on the proximal sides of said bends are positioned on top of said bandage.

23. The method of claim 22 which includes the step of fastening to the top of said bandage the portions of said extension tubes on proximal sides of said bends.

24. The method of claim 22 wherein said extension tubes have flow control means and luer fittings installed on the proximal sides of said bends.

25. The method of claim 21 wherein said extension tubes, including said bends, are flexible.

26. The method of claim 21 wherein the bent extension tubes and said flow diversion means lie in substantially the same plane.

27. The method of claim 21 wherein said extension tubes have a pair of luer fittings fastened to the proximal ends thereof, and a closure cap on each of said luer fittings.

28. The method of claim 21 wherein said connector includes a pair of ferrules on said opposite end thereof, and said extension tubes are fastened to said ferrules.

29. The method of claim 21 wherein said extension tubes have flow control means installed on the proximal sides of said bends in said tubes.

30. The method of claim 21 wherein said flow diversion means forms a pair of internal passageways communicating with the dual lumens of said catheter at said one end of said flow diversion means and with said extension tubes at said opposite end of said flow diversion means.

31. The method of claim 21 wherein the bends in said extension tubes are generally U-shaped.

32. The method of claim 26 wherein the bent extension tubes are attached to the skin of the patient by a first tape extending generally in the direction of the longitudinal axis of the catheter and extending beyond the bends in the extension tubes at one end and beyond the catheter insertion point at the other end.

33. The method of claim 32 which includes a second tape covering the bent extension tube and said first tape and attached to the skin of the patient at opposite ends of the second tape.

34. A dual-lumen catheter assembly comprising
a dual-lumen catheter, and
connecting means attached to the proximal end of said catheter and forming a pair of internal passageways which communicate at one end thereof with the dual lumens in said catheter, said passageways curving back toward the distal end of said catheter so that forces exerted on said connecting means at the other ends of said passageways will tend to move said catheter in a direction opposite that of said exerted forces.

35. The catheter assembly of claim 34 wherein said connecting means comprises a connector fastened to the proximal end of said catheter, and a pair of extension tubes fastened to said connector, said connector forming a pair of internal passageways connecting each of the catheter lumens to one of said extension tubes, and said extension tubes forming said curved passageways.

36. The catheter assembly of claim 34 wherein each of said curved passageways is U-shaped.

37. The catheter assembly of claim 34 wherein said dual-lumen catheter comprises a cylindrical body portion having an internal longitudinal septum forming a pair of elongated lumens having D-shaped cross sections, the distal end of said body portion terminating in a smooth conical tapered tip, one of said lumens extending longitudinally through said tip, and the other lumen terminating at an opening formed in the side wall of said catheter proximally of the distal end of said tip.

38. A blood treatment system comprising
a dual-lumen catheter,
connecting means attached to the proximal end of said catheter and forming a pair of internal passageways which communicate at one end thereof with the dual lumens in said catheter, said passageways curving back toward the distal end of said catheter so that forces exerted on said connecting means at the other ends of said passageways will tend to move said catheter in a direction opposite that of said exerted forces,
a blood treatment unit for receiving blood withdrawn from a patient through one of the lumens of said catheter, purifying the withdrawn blood, and returning the purified blood to the patient through the other lumen of said catheter, and
a pair of flexible tubes connecting said extension tubes to said blood treatment unit.

39. The system of claim 38 wherein said connecting means comprises a connector fastened to the proximal end of said catheter, and a pair of extension tubes fastened to said connector, said connector forming a pair of internal passageways connecting each of the catheter lumens to one of said extension tubes, and said extension tubes forming said curved passageways.

40. The system of claim 38 wherein each of said curved passageways is U-shaped.

41. The system of claim 38 wherein said dual-lumen catheter comprises a cylindrical body portion having an internal longitudinal septum forming a pair of elongated lumens having D-shaped cross sections, the distal end of said body portion terminating in a smooth conical tapered tip, one of said lumens extending longitudinally through said tip, and the other lumen terminating at an opening formed in the side wall of said catheter proximally of the distal end of said tip.

42. A method of preparing a patient for extracorporeal blood treatment comprising the steps of
inserting into a vein selected from the group consisting of the jugular, subclavian and femoral veins of the patient, the distal end portion of a dual-lumen catheter having connecting means attached to the proximal end of said catheter and forming a pair of internal passageways which communicate at one end thereof with the dual lumens in said catheter, said passageways curving back toward the distal end of said catheter so that forces exerted on said connecting means at the other ends of said passageways will tend to move said catheter in a direction opposite that of said exerted forces, and
taping said connector and extension tubes to the skin of the patient.

43. The method of claim 42 wherein said connector and extension tubes are attached to the skin of the patient by a bandage, and the portions of said extension tubes on the proximal sides of said bends are positioned on top of said bandage.

44. The method of claim 43 which includes the step of fastening to the top of said bandage the portions of said extension tubes on the proximal sides of said bends.

45. The method of claim 43 wherein said extension tubes have flow control means and luer fittings installed on the proximal sides of said bends.

46. The method of claim 42 wherein the bends in said extension tubes are permanently set in said tubes.

47. The method of claim 47 wherein said extension tubes, including said bends, are flexible.

48. The method of claim 42 wherein the bent extension tubes and the connector lie in substantially the same plane.

49. The method of claim 42 wherein said extension tubes have a pair of luer fittings fastened to the proximal ends thereof, and a closure cap on each of said luer fittings.

50. The method of claim 42 wherein said connector includes a pair of ferrules on said opposite end thereof, and said extension tubes are fastened to said ferrules.

51. The method of claim 42 wherein said extension tubes have flow control means installed on the proximal sides of said bends in said tubes.

52. The method of claim 42 wherein said Y-shaped connector forms a pair of internal passageways communicating with the dual lumens of said catheter at said one end of the connector and with said extension tubes at said opposite end of the connector.

53. The method of claim 42 wherein the bends in said extension tubes are generally U-shaped.

* * * * *

UNITED STATES PATENT AND TRADEMARK OFFICE
CERTIFICATE OF CORRECTION

PATENT NO. : 4,895,561

DATED : January 23, 1990

INVENTOR(S) : Sakharam D. Mahurkar

It is certified that error appears in the above-identified patent and that said Letters Patent is hereby corrected as shown below:

On Sheet 1, line 1, following "Sheet 1 of", "4" has been replaced with --5--.

On Sheet 2, line 1, following "Sheet 2 of", "4" has been replaced with --5--.

On Sheet 3, line 1, following "Sheet 3 of", "4" has been replaced with --5--.

On Sheet 4, line 1, following "Sheet 4 of", "4" has been replaced with --5--.

Add Drawing Sheet 5 of 5, consisting of Figs. 17 and 18, as shown on the attached page.

Signed and Sealed this

Third Day of November, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO.  : 4,895,561
DATED       : January 23, 1990
INVENTOR(S) : Sakharam D. Mahurkar It is certified that error appears in the above-indentified patent and that said Letters Patent is hereby corrected as shown below:

```
Column 6, line 6, "a direction opposite that of" should
   read -- the same direction as --.

Column 8, line 31, "a direction opposite that of" should
   read -- the same direction as --.

Column 11, line 22, "a direction opposite that of " should
   read -- the same direction as --.
```

Signed and Sealed this

Eighth Day of June, 1993

Attest:

MICHAEL K. KIRK

*Attesting Officer*    Acting Commissioner of Patents and Trademarks

UNITED STATES PATENT AND TRADEMARK OFFICE
CERTIFICATE OF CORRECTION

PATENT NO. : 4,895,561
DATED : January 23, 1990
INVENTOR(S) : Sakharam D. Mahurkar It is certified that error appears in the above-identified patent and that said Letters Patent is hereby corrected as shown below:

Column 6, line 6, "a direction opposite that of" should read -- the same direction as --.

Column 8, line 31, "a direction opposite that of" should read -- the same direction as --.

Column 11, line 22, "a direction opposite that of" should read -- the same direction as --.

Column 11, line 51, "a direction opposite that of" should read -- the same direction as --.

Column 12, line 26, "a direction opposite that of" should read -- the same direction as --.

This certificate supersedes Certificate of Correction issued June 8, 1993.

Signed and Sealed this

Twenty-seventh Day of December, 1994

Attest:

BRUCE LEHMAN

*Attesting Officer*    *Commissioner of Patents and Trademarks*